United States Patent [19]

Dannelly

[11] 4,218,409
[45] Aug. 19, 1980

[54] ENCAPSULATING METHOD

[75] Inventor: Clarence C. Dannelly, Kingsport, Tenn.

[73] Assignee: Eastman Kodak Company, Rochester, N.Y.

[21] Appl. No.: 934,118

[22] Filed: Aug. 16, 1978

Related U.S. Application Data

[62] Division of Ser. No. 766,294, Jul. 7, 1977, Pat. No. 4,123,206.

[51] Int. Cl.² .............................................. A61J 5/04
[52] U.S. Cl. ........................................... 264/4; 264/8
[58] Field of Search ....................................... 264/4, 8

[56] References Cited

U.S. PATENT DOCUMENTS 3,310,612  3/1967  Somerville, Jr. ........................ 264/4
3,423,489  1/1969  Arens et al. ........................... 264/4

Primary Examiner—Donald J. Arnold
Assistant Examiner—James R. Hall
Attorney, Agent, or Firm—John F. Stevens; Daniel B. Reece, III

[57] ABSTRACT

Method is disclosed for forming encapsulated material. Centrifugal force developed by a rotating nozzle having a plurality of radial orifices is used for extruding material to be encapsulated. The nozzle is mounted for rotation about a generally vertical axis and is provided with a circumferential outside surface near its bottom inclined upwardly away from the axis of the nozzle which, when partially submerged in a liquid during rotation, impels a sheet or spray of the liquid along the circumferential surface and shears off successive leading tips of extruded material to form capsules.

7 Claims, 9 Drawing Figures

ENCAPSULATING METHOD

This is a division of application Ser. No. 766,294 filed Feb. 7, 1977 now U.S. Pat. No. 4,123,206.

This invention relates to a method for forming capsules using centrifugal force developed by a rotating nozzle to extrude material for encapsulation.

Centrifugal encapsulating apparatus and methods are known in the art. For example, U.S. Pat. No. 3,015,128 discloses encapsulating apparatus in which a rotating disc is used to impel filler material outwardly toward a rotating cylinder having a bank of encapsulating orifices and films of an encapsulating medium formed across the orifices. The formed capsules are then cast outwardly from the rotating cylinder into a bath which may comprise a moving surface of a hardening liquid disposed in the trajectories. When the capsules are cast into the moving surface of hardening liquid the capsules, complete with their outer films, have already been formed. U.S. Pat. No. 3,310,612 relates to apparatus for forming larger capsules with generally similar equipment as disclosed in U.S. Pat. No. 3,015,128.

In accordance with the present invention, improved centrifugal encapsulating method is provided. A nozzle mounted for rotation about a generally vertical axis centrifugally extrudes material through a plurality of radial orifices. The nozzle is partially submerged in a liquid and is provided with a lower surface which, when rotated partially submerged in liquid, impels a spray or sheet of the liquid along this surface to intercept successive leading tips of extruded material, thereby severing and hardening the outer portions of the tips. Hardening of the surfaces of the tips is caused by contact with the liquid and/or atmosphere, and may be due to a change in temperature, polymerization, crosslinking, etc. Such apparatus and method combine simplicity with a wide performance capability of capsule size, material, speed, operating parameters and efficiency.

It is an object of the present invention to provide a method for centrifugally forming encapsulated material.

It is another object of this invention to provide simple a method for forming generally round capsules at a high speed, It is still another object of this invention to provide an efficient process having a wide range of capabilities for forming capsules.

Other objects and advantages of the present invention will appear hereafter.

In the drawings which illustrate a specific embodiment of the invention:

Figure 1:
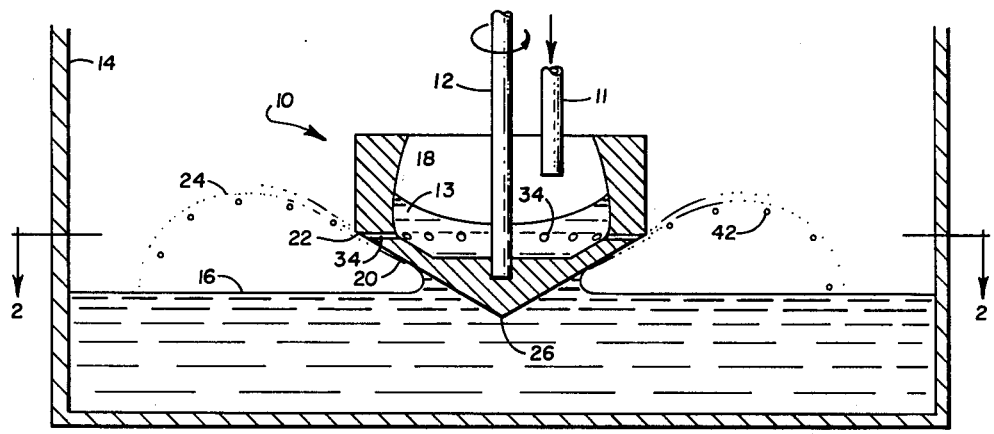
FIG. 1 is a cross-sectional elevation view, partially in schematic, illustrating one embodiment of the encapsulating apparatus and method according to my invention.

Referring to FIG. 1, nozzle 10 is fixed to shaft 12 which is mounted for rotation about a generally vertical axis. Suitable means for rotating the nozzle 10 in this position such as an electric motor, speed reducer, bearings, etc. (not shown), are provided and are known to those skilled in the art. A suitable vessel 14 is provided for placement under nozzle 10 to maintain a body of liquid 16 in contact with a portion of nozzle 10.

Figure 2:
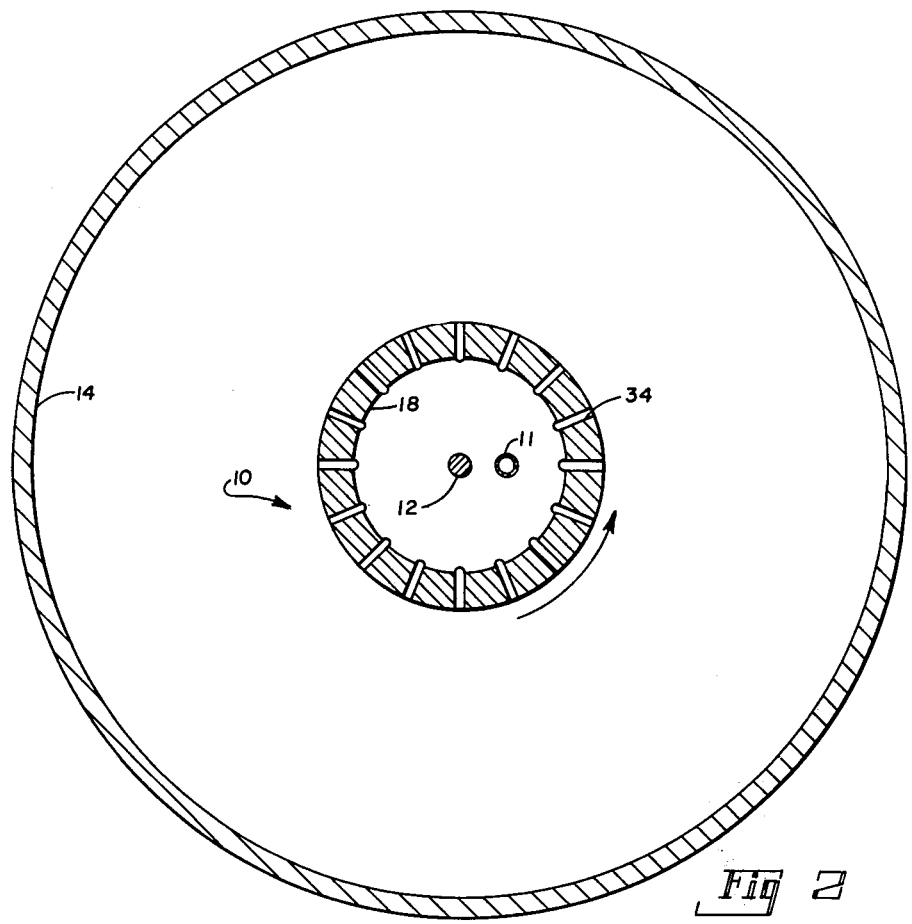
FIG. 2 is a plan view of the apparatus illustrated in FIG. 1.

Nozzle 10 may be fabricated from any suitable material such as metal, ceramic, plastic, wood, or the like which is capable of withstanding centrifugal forces of rotation. The nozzle 10 is generally circular in cross section along a plane perpendicular to shaft 12 as shown in FIG. 2. Shaft 12 may be fixed to nozzle 10 by any convenient means such as, for example, threading, press fit, key, etc.

As illustrated in FIGS. 1 and 2, nozzle 10 is provided with a generally conical, or truncated conical outside circumferential surface 20 inclined upwardly as the radius increases. Circumferential surface 20 extends from the bottom or closed end of nozzle 10, to a circumferential ring 22 on the sidewall of nozzle 10. The inclination of circumferential surface 20 is such that when nozzle 10 is rotated about a generally vertical axis with the lower portion submerged in a body of liquid 16, centrifugal force and surface tension of liquid 16 combine to impel a sheet or spray 24 upwardly along the surface thereof. The nozzle 10 is partially submerged in liquid 16. That is, the liquid level, while the nozzle 10 is at rest, would extend at lease one quarter of the axial distance from the bottom of the nozzle to the orifices, and no higher than the outer ports of the orifices.

Figure 3:
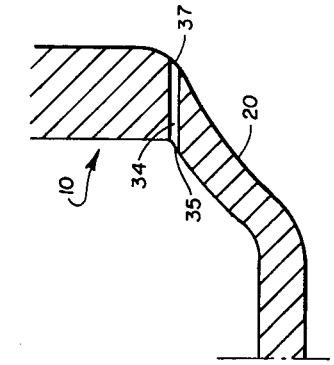
FIGS. 3 and 4 illustrate partial sectional views of nozzles suitable for use according to this invention.
Figure 4:
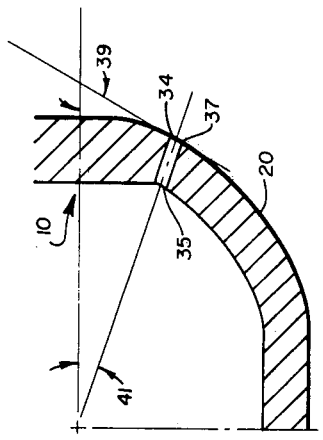

The inclined circumferential surface 20 is generally smooth and may assume a variety of shapes. Several of the more conventional shapes are shown in the drawings. For example, this surface need not extend to the axis of rotation and terminate at a point 26. The inclined section may be somewhat concave or convex as illustrated in FIGS. 3 and 4. Nozzle 10 should be designed with regard to intended speed of rotation, diameter, viscosity and surface tension of liquid 16, such that upon rotation of nozzle 10, sheet of liquid 24 will be impelled along the inclined surface 20 to separate leading tips of extruded material from the outer ports of the orifices.

Nozzle 10 is provided with at least one, and preferably a plurality of spaced orifices 34 extending generally radially through the wall and usually on a circumferential line. Orifices 34 provide for the capsule material 13 to be extruded by centrifugal force when the nozzle 10 is rotated. Inside ports are therefore positioned at, or near, the portion of greatest inside diameter.

The inside wall 18 of nozzle 10 is preferably tapered inwardly toward the open end to reduce the likelihood of material to be encapsulated from escaping as the container 10 is rotated. Material to be encapsulated may be conveyed to nozzle 10 continuously or batchwise through line 11.

Figure 5:
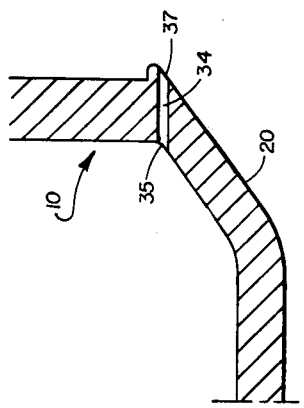
FIG. 5 illustrates a modification in the wall design of a nozzle according to this invention.
Figure 6:
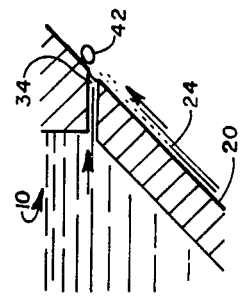
FIGS. 6-9 inclusive illustrate formation of capsules from material in accordance with this invention.

The orifices 34 extend through the wall of the nozzle and are positioned such that material 13 will develop sufficient centrifugal force during rotation to extrude completely through the orifice as shown in FIGS. 6-9 inclusive. Thus, the orifices must at least have a substantial radial component, and preferably extend generally in a radial direction from the axis as shown in FIGS. 3 and 5. The interior port 35 of the orifices must be positioned to communicate with the material 13 when the nozzle 10 is rotated at operating speed. The orifices may be positioned to have an axial component, i.e., inclined downwardly in the radial direction in its operating position as illustrated in FIG. 4. Such inclination (angle 41) should not be greater than about 70° from horizontal. Preferably, angle 41 is near zero, but angles up to about 30° have no substantial adverse effect on performance. The outer port 37 of the orifices must be positioned such that the sheet of liquid moving across the surface 20 intercepts the capsule during formation and separates it from the outer port 37. Thus, the plane in which the outer port generally lies should make an angle (angle 39) of between about 70° and about 90° with the horizontal when the nozzle is in operating position.

FIG. 5 is similar to FIGS. 3 and 4 but illustrates a variation in the shape of the nozzle 10. Immediately above the ring of orifices 34 a ledge is provided which allows formed capsules to break away easily from the outside port 37 of orifices 34. Such capsules are thus allowed to break away sharply from the nozzle and are better assured of clean separation.

Figure 7:
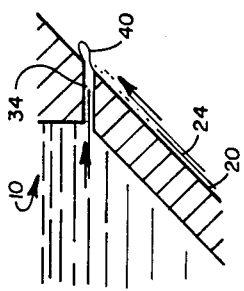
Figure 8:
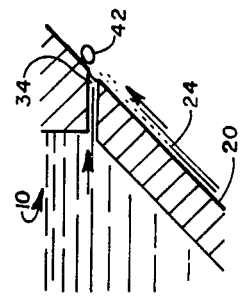
Figure 9:
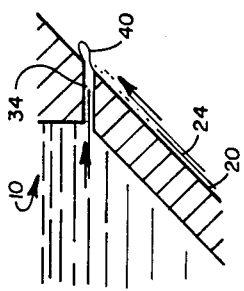

FIGS. 6–9 inclusive illustrate the formation of capsules by means of the present invention. Centrifugal force exerted on liquid material 13 causes such material to be extruded through the orifices 34 as nozzle 10 is rotated. Simultaneously, centrifugal force and surface tension of liquid 16 cause a sheet 24 of such liquid to be impelled along the inclined surface 20 as indicated by the arrow. In FIG. 7, the leading tip 40 of material 13 is being deformed by the sheet of liquid. In FIG. 8, force of the sheet of liquid is about to separate the leading tip 40. In FIG. 9, the leading tip has been separated and is being carried away as a separate capsule 42. The next leading tip of the extrudate is approaching a point where the sequence will be repeated. Completed capsules may be allowed to fall by gravity back into the vessel 14 containing liquid 16 for recovery.

The material 13 to be encapsulated must be capable of flowing through the orifices 34 and forming "droplets" (leading tips 40) held intact by surface tension until separated by sheet 24. Liquid 16 must be capable of being impelled along inclined surface 20 past the orifices 34 to separate successive leading tips 40 of extrudate. Also, contact of the material 13 with air and/or liquid 16 must harden the surface of the formed capsules. Such hardening may be accomplished by either physical or chemical means, including:

(a) The material 13 is capable of gelling by a change in temperature (usually by cooling) and liquid 16 is maintained at a different temperature;
(b) Liquid 16 is capable of polymerizing or crosslinking the surface film of the material 13; or
(c) Liquid 16 otherwise solidifies into a film around the material to be encapsulated.

The construction and operation of the centrifugal encapsulating apparatus of this invention, as well as certain of the advantages and desirable features provided thereby, will be clearly understood in view of the foregoing description. However, a summary of the variables within the control of the operator which may affect the characteristics of the finished capsules, as well as a summary of certain of the inherent operational characteristics of the apparatus, will be helpful in this regard. In the following discussion, unless otherwise stated, it is assumed that operating variables, other than the particular variable being discussed, are maintained constant so that the effect on the capsule characteristics resulting from changing the particular operating variable in the direction indicated can be demonstrated. As will be understood, it may be necessary to change one or more of these operation variables in order to provide capsules having desired characteristics when operating under a given set of conditions.

SPEED OF ROTATION OF THE NOZZLE

The speed of rotation of the nozzle affects the size and rate of capsule formation. That is, with other factors remaining constant, increased rotational speed results in the production of smaller capsules at a higher rate of formation while decreased rotational speed of the cylinder results in production of larger capsules at a slowed rate of formation. Rim speeds within the range of about 200 inches per minute to about 50,000 inches per minute are normal.

ORIFICE SIZE

The capsule size is affected by the size of the encapsulating orifices. Smaller orifices result in smaller sized capsules, while larger orifices result in larger sized capsules. However, control of other variables such as rotational speed of the nozzle, viscosity of material 13, etc., permit the formation of capsules in a relatively wide range with any given orifice size. Generally speaking, smaller sized orifices require greater speeds of rotation. Generally, orifices will be within the range of about 0.05 inch to about 0.5 inch. The capacity of this apparatus can easily be increased, for example, by increasing the number of encapsulating orifices.

VISCOSITY OF LIQUID MATERIAL TO BE ENCAPSULATED

Variations in viscosity affect several characteristics of the capsules, particularly the production rate, size, capsule payload, and rotational speed required. Higher viscosities tend to reduce both the size and the rate of production, while lower viscosities tend to increase both the size and the rate of production. Normally, the viscosity of material 13 will be within the range of about 50 cps. to about 30,000 cps.

SURFACE TENSION OF THE MATERIAL TO BE ENCAPSULATED

Variations in surface tension of the material 13 have the same general effect as variations in viscosity. Normally, the surface tension of material 13 will be within the range of about 26 dynes per centimeter to about 100 dynes per centimeter.

The viscosity and surface tension of liquid 16 affect the formation of the liquid sheet 24. Normally, the viscosity will be within the range of about 0.5 cps. to about 1500 cps. and have a surface tension of about 24 dynes per centimeter to about 90 dynes per centimeter. The liquid level required depends somewhat upon the anticipated speed of rotation and surface tension, but normally is between ⅛ and ¾ of the distance from the bottom of the nozzle to the level of the orifice.

The following example is submitted for a better understanding of the invention.

EXAMPLE

Apparatus similar to that illustrated in FIGS. 1 and 2 is used in this example. The nozzle, made of a ceramic material has an outside diameter of 3.0 inches, an inside diameter at the ring of orifices of 2.75 inches, an angle of orifice to horizontal of 0 degrees (angle 41 in FIG. 4). The plane in which outer port 37 lies makes an angle of 80 degrees with horizontal (angle 39 in FIG. 4). The nozzle contains 36 orifices of 1/16 inch diameter equally spaced circumferentially around the nozzle.

The nozzle is submerged 0.5 inch in a body of butyl acetate such that the liquid level at rest is about halfway between the extreme bottom of the nozzle and the ring of orifices. The butyl acetate has a viscosity of 0.7 cps., 24.7 dynes per centimeter surface tension, and a temperature of 25° C. The nozzle is rotated at a rim speed of 9000 inches per minute, and a 4% solids solution of agar in water heated to 60° C. is charged into the nozzle. The agar solution has a viscosity of 2450 cps., a surface tension of 73.4 dynes per centimeter, and a temperature of 60° C. The butyl acetate is impelled along the inclined surface as a sheet and intercepts the tips of material being extruded to separate them. Capsules are formed by their contact with the butyl acetate and/or the surrounding atmosphere. In this case, a self-supporting film of the agar gels upon contact with matter of a cooler temperature. Capsules of 0.12 inch diameter are formed at a rate of $>10,000$ per minute.

Unless otherwise specified, all ratios and percentages are on a weight basis.

The invention has been described in detail with particular reference to certain preferred embodiments thereof, but it will be understood that variations and modifications can be effected within the spirit and scope of the invention.

I claim:

1. A method of forming liquid filled capsules comprising (a) flowing a droplet-forming fluid material, around which capsules are to be formed, into a nozzle supported for rotation about a vertical axis, said nozzle having a wall with an outside surface inclined upwardly with an increasing radius, and at least one orifice extending radially through said wall, (b) placing said nozzle below the surface of a body of hardenable liquid having a viscosity of about 0.5–1500 centipoises wherein a portion of said inclined surface of said nozzle is submerged in said liquid with said orifice above the liquid surface level when said liquid is at rest, (c) rotating said nozzle to extrude said material as droplets through the orifice by centrifugal force and to cause a sheet of said liquid to be impelled across at least a portion of the inclined surface of said nozzle and across said orifice at which a portion of said sheet separates and forms a film surrounding each of said formed droplets, (d) causing said liquid film surrounding said droplets leaving said orifice to harden to contact with air or said liquid to form liquid-filled capsules, and (e) collecting filled capsules in said body of liquid.

2. The method of claim 1 where in step (a) the level of said body of liquid at rest is at least about ¼ of the axial distance from the bottom of said nozzle to the orifice and no higher than the orifice.

3. The method of claim 1 where in step (c) said nozzle is rotated at a rim speed of about 2000–50,000 inches per minute.

4. The method of claim 1 where in step (c) said liquid film surrounding said droplets is hardened by polymerization or cross-linking.

5. A method of forming liquid-filled capsules which comprises the steps of (a) flowing a droplet-forming fluid material, around which capsules are to be formed, into a nozzle supported for rotation about a vertical axis, said nozzle having a wall with an outside surface inclined upwardly with an increasing radius and at least one orifice extending radially through said wall, (b) placing said nozzle below the surface of a body of liquid having a viscosity of about 0.5–1500 centipoises wherein a portion of said inclined surface of said nozzle is submerged in said liquid with said orifice above the liquid surface level when said liquid is at rest, (c) rotating said nozzle to extrude said material as droplets through the orifice by centrifugal force, and to cause a sheet of said liquid to be impelled across at least a portion of the inclined surface of said nozzle and across said orifice at which a portion of said sheet separates said extruded material into droplets, (d) causing the surface of said droplets to gel and harden as a film by contact with air or said liquid maintained at a temperature different from that of said droplet-forming fluid material, and (e) collecting said capsules in said body of liquid.

6. The method of claim 5 where in step (b) the level of said body of liquid at rest is at least about ¼ of the axial distance from the bottom of said nozzle to the orifice and no higher than the orifice.

7. The method of claim 5 where in step (c) said nozzle is rotated at a rim speed of about 2000–50,000 inches per minute.

* * * * *